US00PP33132P3

(12) United States Plant Patent
Hansen

(10) Patent No.: US PP33,132 P3
(45) Date of Patent: Jun. 1, 2021

(54) ***MONARDA* PLANT NAMED 'LEADING LADY ORCHID'**

(50) Latin Name: ***Monarda* hybrid**
Varietal Denomination: Leading Lady Orchid

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,548

(22) Filed: Nov. 30, 2018

(65) Prior Publication Data

US 2020/0390016 P1 Dec. 10, 2020

(51) Int. Cl.

| | |
|---|---|
| ***A01H 5/02*** | (2018.01) |
| ***A01H 6/50*** | (2018.01) |
| ***A01H 6/14*** | (2018.01) |

(52) U.S. Cl.
USPC ..... Plt./455
CPC ..... *A01H 6/14* (2018.05)

(58) Field of Classification Search
USPC ..... Plt./263.1, 455
See application file for complete search history.

*Primary Examiner* — Susan McCormick Ewoldt
*Assistant Examiner* — Karen M Redden

(57) ABSTRACT

The new and distinct cultivar of ornamental cultivar of hybrid ornamental Bee Balm plant named *Monarda* 'Leading Lady Orchid' with slightly-glossy, powdery mildew-tolerant foliage, flower heads of magenta-pink flowers with lower petals accented by dark fuchsia spotting, each globular head subtended by wine-colored bracts. Flowering in dense verticils beginning about two weeks earlier than typical *Monarda didyma* cultivars. Flowers of side branches stretching above initial globular heads extends the fresh appearance over along period. The plant habit is short, compact and winter-hardy, useful in the landscape as a specimen, en masse, or as a containerized plant.

1 Drawing Sheet

Botanical designation and cultivar denomination:
Botanical classification: *Monarda* hybrid.
Variety denomination: 'Leading Lady Orchid'.

STATEMENT REGARDING PRIOR DISCLOSURES UNDER 37 CFR 1.77(B)(6)

The first public disclosure of the claimed plant, in the form of a sale, was made by Walters Gardens, Inc. on Jul. 16, 2018. Prior to that, on Dec. 1, 2017 the claimed plant was displayed with a photograph and brief description in a website operated by Walters Gardens, Inc., who obtained the plant and all information relating thereto, from the inventor. No plants of *Monarda* 'Leading Lady Orchid' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct cultivar of Bee balm, botanically known as *Monarda* 'Leading Lady Orchid', and hereinafter also referred to solely by the cultivar 'Leading Lady Orchid' or the "new plant." *Monarda* 'Leading Lady Orchid' was the result of a controlled insect pollination in the summer of 2012 in an isolation block at a wholesale perennial nursery in Zeeland, Mich., USA. The female parent is a proprietary *didyma* times *bradburiana* hybrid known as H10-26-09 and the specific male parent is unknown but would have been a sibling with the same parentage. The new plant was separated out for further evaluation in the summer of 2014 in the full sun trial gardens of the same nursery and assigned the breeder code 12-59-8. The new plant is the result of a planned breeding program of the inventor to produce new colors of flowers with superior mildew resistance, and improved compact habit. The new plant has been asexually propagated since 2015 by stem cuttings at the same nursery in the greenhouses in Zeeland, Mich., and the subsequent generations of asexually propagated plants found to be stable and identical to the original selection.

BRIEF SUMMARY OF THE PLANT

*Monarda* 'Leading Lady Orchid' is unique from its parents and all other Bee Balm plants known to the inventor. The nearest comparison cultivars known to the inventor are 'Leading Lady Plum' U.S. Plant Pat. No. 26,447 and 'Leading Lady Lilac' U.S. Plant Pat. No. 26,431. 'Leading Lady Lilac' has lighter flowers of a lilac-purple color. 'Leading Lady Plum' has flowers of a more magenta-purple color. The female parent has similar darker reddish-purple accent spots in the flower like that of *Monarda* 'Leading Lady Orchid', but it is lighter in background petal color and is more spreading and taller in habit than the new plant. All of the potential male parents have spotted petals with a lighter lilac-color.

The new plant *Monarda* 'Leading Lady Orchid' is distinct from all Bee Balm plants known to the inventor. The following are traits of *Monarda* 'Leading Lady Orchid' that in combination distinguish it from all other Bee balm known to the inventor:

1. Dark-green, slightly-glossy, powdery mildew-tolerant foliage.

2. Short, compact, clumping, winter-hardy habit.
3. Compact, magenta-pink flowers for a long period beginning late spring, at least two weeks earlier than typical *Monarda didyma* cultivars.
4. Inside of lower flower petals accented by rows of darker fuchsia spots.
5. Flowers in dense verticils with side branches flowering above initial flowers providing fresh flowering appearance.

BRIEF DESCRIPTION OF THE DRAWINGS

The photographs of the new plant demonstrate the unique traits of *Monarda* 'Leading Lady Orchid' and the overall appearance of the plant at two-years old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
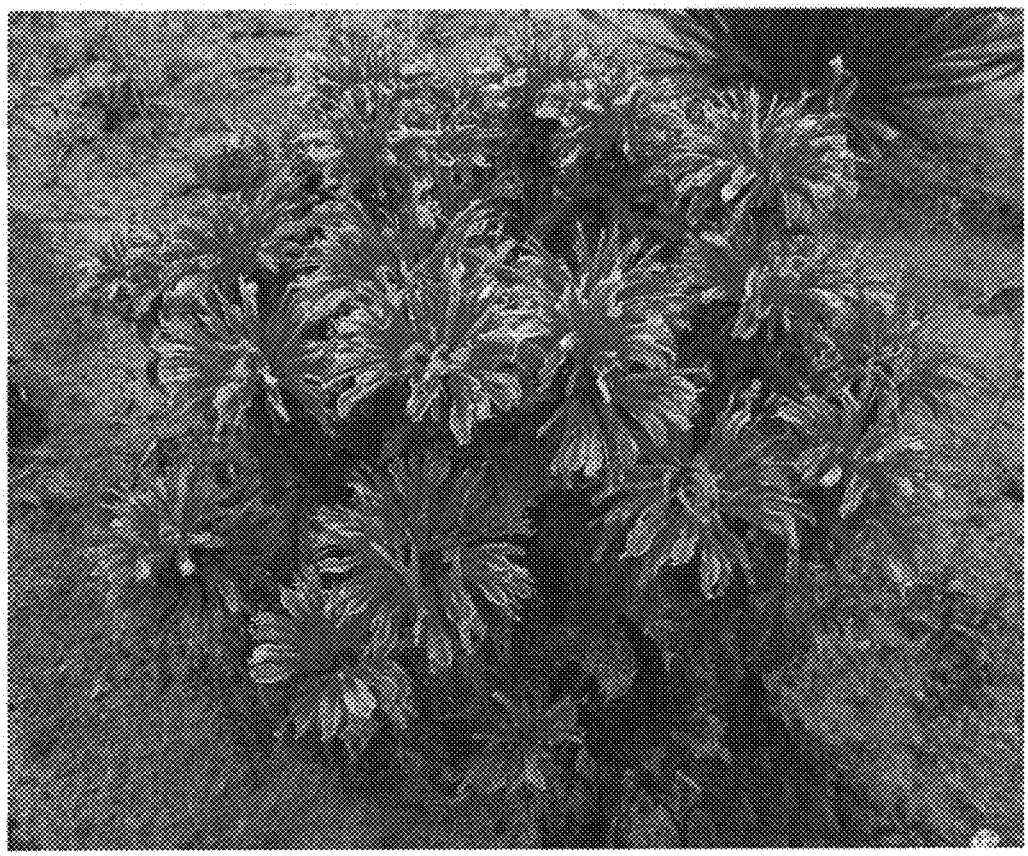
FIG. 1 shows the habit of the new plant in flower.
Figure 2:
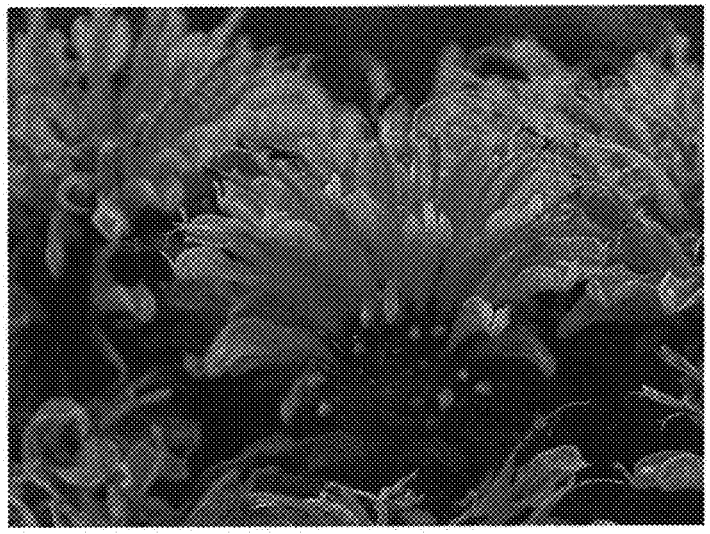
FIG. 2 shows a close-up of the flower of the new plant.

The following descriptions and color references are based on the 2015 edition of The Royal Horticultural Society Colour Chart except where common dictionary terms are used. *Monarda* 'Leading Lady Orchid' has not been observed under all possible environments. The phenotype may vary slightly with different growing environments such as temperature, light, fertility, soil pH, moisture and maturity levels, but without any change in the genotype. The following observations and size descriptions are based on two-year-old, full-sun, trial garden-grown plants and greenhouse grown plants at a nursery in Zeeland, Mich. with limited supplemental fertilizer and water as needed but without plant growth regulators or pinching.

Botanical classification: *Monarda didyma* x *Monarda bradburiana;*

Parentage: The female (seed) parent is H10-26-09, an unreleased proprietary selection of *Monarda didyma* times *M. bradburiana*; the male (pollen) parent is an unknown, unreleased, proprietary sibling of the female parent;

Plant habit: Hardy herbaceous perennial, compact, producing multiple stems spreading by short rhizomes near the base of the stems; foliage up to 26.0 cm tall, flowering to 35.0 cm tall and wide; flowering begins late spring in Michigan and continuing for about 5 to 9 weeks;

Propagation: Stem cuttings;

Time to produce finished crop in 3.8 liter pots: About 7 to 9 weeks; moderate rate of growth;

Root: Fine, fibrous and freely branching; color creamy white to tan depending on soil type;

Leaves: Simple; lanceolate; opposite; margin serrated and ciliolate; puberulent above and below; lustrous above, semi-lustrous to matte below; acute apex; cordate to rounded base; to about 9.0 cm long and 4.0 cm wide, average about 6.8 cm long and 3:5 cm wide;

Leaf color: Young expanding leaves adaxial nearest RHS 137B with blush of nearest RHS N186C, abaxial nearest RHS 147C; older leaves adaxial blend between RHS 139A and RHS 137A and abaxial nearest RHS 147B below;

Foliage fragrance: Pleasant herbal;

Veins: Pinnate; pubescent abaxial with glabrous above, slightly sunken above and raised below;

Vein color: Adaxial midrib nearest RHS 145C, lateral pinnate veins nearest RHS 145B and secondary veins nearest RHS 137A; abaxial midrib nearest RHS 145C with lateral pinnate veins nearest RHS 146D and secondary veins nearest RHS 137B;

Petiole: Pubescent, slightly concaved above; to about 5.0 mm long and 3.0 mm across at base;

Petiole color: Adaxial nearest RHS 146C and abaxial nearest RHS 146D;

Stems: Quadrangular; puberulent; about 4.0 mm across at base; about 40 per plant; naturally branched at upper nodes; average 1.7 cm between nodes greater distally; 15 to 18 nodes per stem; average length about 28 cm;

Stem color: Nearest RHS 146A;

Flowers: Single labiate flowers arranged in mostly terminal verticils forming globular head about 7.0 cm across and 4.0 cm tall opening from the center and progressing outwardly and down; attitude upwardly to outwardly; individual flowers to about 39.0 mm long to exserted stigma and about 5.0 mm across; individual flowers persisting about 5 days in Michigan; numerous, about 200 flowers per terminal head, fewer per axillary head;

Flower fragrance: Moderately spicy;

Buds one to two days prior to opening: Narrowly oblanceolate, arcuate downward; about 22.5 mm long and 3.0 mm across and 5.5 mm tall; between RHS NN74C and RHS N74C in the middle and dorsal distal region lighter than RHS N74D;

Petals: Labiate; arcuate downward; base fused into tube; split in two in the distal 1.2 cm with upper lip fused into a hood about 30.0 mm long and 3.0 mm across; lower lip about 35.0 mm long comprising three lobes including two side lobes about 1.0 mm long with rounded apex and center lobe about 4.5 mm long bifid in the distal 1.0 mm; both petals glandular and pubescent on outer surfaces with fine hairs the same color as petals, both petals glabrous on inner surfaces; self-cleaning;

Petal color: Upper hood petal on both abaxial and adaxial surfaces between RHS N74C and RHS NN74C lightening with maturity to lighter than RHS NN74D; lower petal adaxial and abaxial between RHS 75D and RHS NN74D with spots in the strips about 0.5 mm diameter of nearest RHS 71A; fused corolla tube abaxial between RHS N74C and RHS NN74C with basal 5.0 mm nearest RHS 155B, adaxial nearest RHS 75C with basal 5.0 mm nearest RHS 155B;

Filaments: Two, curved downward, about 1.4 cm long by 0.5 mm diameter fused to petal about 1.4 cm from base; color nearest RHS 76B;

Anther: Oblong elliptic, dorsifixed, longitudinal; 2.2 mm long by 1.0 mm wide; color nearest RHS N186A;

Pollen: Abundant, elliptic to globose, less than 0.1 mm; color nearest RHS 18A;

Pistil: One per flower; protruding about 7.0 mm beyond upper petal when mature;

Style: About 3.8 cm long and less than 0.5 mm diameter; color nearest RHS 76A distally and base nearest RHS NN155D;

Stigma: Bifid in the distal 2.0 mm; about 0.2 mm in diameter; color nearest RHS 76A;

Ovary: About 1.0 mm across by 0.7 mm tall; color between RHS 143D and RHS 144B;

Sepals: Five, apiculate apex; base fused forming calyx tube; margin ciliolate; about 10.0 mm long and 2.0 mm diameter, fused in basal 8.0 mm to form a tube; glandular abaxial surface and glabrous adaxial; persistent;

Sepal color: Adaxial and abaxial distal two-thirds between RHS N186D and RHS 187C, both adaxial and abaxial base nearest RHS 139C;

Foliar bracts: Usually two rows of six each in number; below verticils; lanceolate distal row and ovate to deltoid proximal row; apex acuminate to acute; base sessile, truncate; margin entire; adaxial glabrous, abaxial puberulent; lower row of bracts about 18.0 mm long and 15.0 mm wide at base; upper row of bracts, about 14.0 mm long and 4.5 mm wide;

Foliar bract color: Color of both rows similar, adaxial and abaxial variable with both nearest RHS N186D and RHS 139A;

Peduncle: Pubescent, stiff, strong, erect, squared in cross-section to about 0.4 cm across and average 28 cm long; about 30 per plant; naturally branched at nodes; average 1.7 cm between nodes; 15 to 18 nodes per stem;

Peduncle color: Between RHS 146A and RHS 146B;

Pedicel: About 1.0 mm long and 0.5 mm diameter; color nearest RHS 145B;

Fruit: Single nutlet, elliptical, about 1.3 mm long and 0.7 mm wide; color nearest RHS 200C;

Hardiness: The new plant grows best with plenty of moisture and adequate drainage; hardy to at least from USDA zone 4 through 8.

Disease and pest resistance: Demonstrated greater than average powdery mildew tolerance in side by side comparison with other *Monarda*.

I claim:

1. A new and distinct cultivar of hybrid ornamental Bee Balm plant, *Monarda* 'Leading Lady Orchid', as herein described and illustrated.

* * * * *